(12) United States Patent
Hoff et al.

(10) Patent No.: US 10,092,297 B2
(45) Date of Patent: Oct. 9, 2018

(54) TISSUE COMPRESSION DEVICE WITH FIXATION AND TENSION STRAPS

(71) Applicant: Medtronic Vascular, Inc., Santa Rosa, CA (US)

(72) Inventors: Mark Hoff, Windsor, CA (US); Sanaz Saatchi, San Francisco, CA (US); Brian Joseph Mason, Palo Alto, CA (US); John Lai, San Bruno, CA (US); Remy O'Leary Pieron, San Francisco, CA (US); Yusuke Miyashita, San Mateo, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 554 days.

(21) Appl. No.: 14/262,336

(22) Filed: Apr. 25, 2014

(65) Prior Publication Data

US 2015/0305958 A1    Oct. 29, 2015

(51) Int. Cl.
*A61B 17/132* (2006.01)
*A61B 17/08* (2006.01)
*A61B 17/00* (2006.01)

(52) U.S. Cl.
CPC ........ *A61B 17/1325* (2013.01); *A61B 17/085* (2013.01); *A61B 17/132* (2013.01); *A61B 17/1322* (2013.01); *A61B 2017/00407* (2013.01)

(58) Field of Classification Search
CPC .............. A61B 17/132; A61B 17/1322; A61B 17/1325; A61B 17/12009; A61B 17/12; A61B 2017/12018; A61B 2017/12004; A61B 17/135; A61B 17/1355; A61B 17/0273; A61B 17/0269; A61B 17/0246; A61F 13/00029; A61F 13/00; A61F 13/02; A61F 13/023; A61F 13/0246;
(Continued)

(56) References Cited

U.S. PATENT DOCUMENTS

| | | |
|---|---|---|
| 721,162 A | 2/1903 | Denain |
| 1,870,052 A | 11/1930 | Jones |
| 1,824,516 A | 9/1931 | Tyvand |

(Continued)

FOREIGN PATENT DOCUMENTS

| | | |
|---|---|---|
| CN | 10192666 | 12/2010 |
| CN | 203059815 | 7/2013 |

(Continued)

OTHER PUBLICATIONS

Air-Band Radial Compression Device, Instructions for use, pp. 1-88, 2013.

*Primary Examiner* — Christopher L Templeton
(74) *Attorney, Agent, or Firm* — Medler Ferro Woodhouse & Mills PLLC

(57) ABSTRACT

Tissue compression devices with a combination of fixation and tension straps and methods of using the same are described herein. The tissue compression devices include a combination of fixation and tension straps that are used together to fix or attach the tissue compression device over selected tissue at a selected location on a patient and to apply pressure to the selected tissue. In one or more embodiments, the fixation straps are used to fix or attach the tissue compression device and the tension straps are used to provide tension that is converted to pressure on the selected tissue.

20 Claims, 3 Drawing Sheets

(58) Field of Classification Search
CPC ........ A61F 13/0243; A61F 2013/00089; A61F 2013/00468; A61F 2013/00174
See application file for complete search history.

(56) References Cited

U.S. PATENT DOCUMENTS

| | | | |
|---|---|---|---|
| 2,271,927 A | 6/1938 | Saighman | |
| 2,316,158 A | 4/1943 | Eschner | |
| 2,332,107 A | 10/1943 | Nieburgs | |
| 2,344,021 A | 3/1944 | Bouziane | |
| 2,387,642 A | 10/1945 | Calhoun | |
| 3,171,410 A | 3/1965 | Towle, Jr. et al. | |
| 3,620,209 A | 11/1971 | Kravitz | |
| 3,654,931 A | 4/1972 | Hazlewood | |
| 4,005,709 A | 2/1977 | Laerdal | |
| 4,297,996 A | 11/1981 | Uriza | |
| 4,834,802 A | 5/1989 | Prier | |
| 5,176,703 A * | 1/1993 | Peterson | A61B 17/085 602/41 |
| 5,269,803 A | 12/1993 | Geary et al. | |
| 5,307,811 A * | 5/1994 | Sigwart | A61B 17/132 600/481 |
| 5,507,721 A | 4/1996 | Shippert | |
| 5,584,802 A * | 12/1996 | Hess | A61F 13/061 602/26 |
| 5,601,597 A | 2/1997 | Arrowood et al. | |
| 5,660,182 A | 8/1997 | Kuroshaki et al. | |
| 5,690,610 A | 11/1997 | Ito et al. | |
| 5,695,520 A | 12/1997 | Bruckner et al. | |
| 5,709,647 A | 1/1998 | Ferber | |
| 5,728,120 A | 3/1998 | Shani et al. | |
| 5,792,173 A | 8/1998 | Breen et al. | |
| 5,873,890 A | 2/1999 | Porat | |
| 5,968,072 A | 10/1999 | Hite et al. | |
| 6,068,646 A | 5/2000 | Lam | |
| 6,077,241 A | 6/2000 | Fareed | |
| 6,217,601 B1 | 4/2001 | Chao | |
| 6,336,901 B1 | 1/2002 | Itonaga et al. | |
| 6,361,496 B1 | 3/2002 | Zikorus et al. | |
| 6,503,266 B1 | 1/2003 | Sjogren et al. | |
| 6,506,206 B1 | 1/2003 | Guzman et al. | |
| 6,593,508 B1 | 7/2003 | Harder | |
| 6,663,653 B2 | 12/2003 | Akerfeldt | |
| 6,694,821 B2 | 2/2004 | Yamakoshi et al. | |
| 6,746,470 B2 | 6/2004 | McEwen et al. | |
| 6,752,820 B1 | 6/2004 | Hafemann | |
| 6,758,821 B2 | 7/2004 | Itonaga et al. | |
| 6,827,727 B2 | 12/2004 | Stalemark et al. | |
| 6,833,001 B1 | 12/2004 | Chao | |
| 7,135,032 B2 | 11/2006 | Akerfeldt | |
| 7,247,163 B2 | 7/2007 | Akerfeldt | |
| 7,329,270 B2 | 2/2008 | Akerfeldt et al. | |
| 7,445,625 B2 | 11/2008 | Akerfeldt | |
| 7,498,477 B2 | 3/2009 | Wade et al. | |
| 7,582,102 B2 | 9/2009 | Heinz et al. | |
| 7,637,921 B2 | 12/2009 | Akerfeldt et al. | |
| 7,652,190 B2 | 1/2010 | Johnson | |
| 7,763,046 B2 | 7/2010 | Schouten et al. | |
| 7,780,612 B2 | 8/2010 | Ross et al. | |
| 7,927,295 B2 | 4/2011 | Bates et al. | |
| 8,034,009 B2 | 10/2011 | Bates et al. | |
| 8,277,483 B2 | 10/2012 | Teeslink et al. | |
| 8,353,927 B2 | 1/2013 | Lampropoulos et al. | |
| 8,439,943 B2 | 5/2013 | Chao | |
| 8,481,805 B2 | 7/2013 | Wada et al. | |
| 8,524,974 B2 | 9/2013 | Wada et al. | |
| 8,657,850 B2 | 2/2014 | McNeese | |
| 8,759,603 B2 | 6/2014 | Wada et al. | |
| 8,834,517 B2 | 9/2014 | Croushorn et al. | |
| 8,845,680 B2 | 9/2014 | Lampropoulos et al. | |
| 8,870,781 B2 | 10/2014 | Lee et al. | |
| D733,305 S | 6/2015 | Miyashita et al. | |
| 2003/0055453 A1 | 3/2003 | Akerfledt | |
| 2003/0114881 A1 | 6/2003 | Stalemark et al. | |
| 2003/0139696 A1 | 7/2003 | Boukanov et al. | |
| 2003/0199922 A1 | 10/2003 | Buckman | |
| 2004/0039413 A1 | 2/2004 | Akerfeldt et al. | |
| 2004/0068290 A1 | 4/2004 | Bates et al. | |
| 2004/0092999 A1 | 5/2004 | Lojewski | |
| 2004/0143289 A1 | 7/2004 | Zahler et al. | |
| 2004/0243044 A1 * | 12/2004 | Penegor | A61B 17/0057 602/48 |
| 2005/0131326 A1 | 6/2005 | Bates et al. | |
| 2006/0025807 A1 * | 2/2006 | Licata | A61B 17/132 606/203 |
| 2007/0191881 A1 | 8/2007 | Amisar et al. | |
| 2007/0293888 A1 | 12/2007 | Harren et al. | |
| 2008/0125684 A1 | 5/2008 | Nardi et al. | |
| 2008/0216213 A1 | 9/2008 | Lin et al. | |
| 2008/0312682 A1 | 12/2008 | Shams et al. | |
| 2009/0234261 A1 | 9/2009 | Singh | |
| 2009/0318952 A1 | 12/2009 | Bates et al. | |
| 2009/0318953 A1 | 12/2009 | Bates et al. | |
| 2011/0028934 A1 | 2/2011 | Buckman | |
| 2011/0130739 A1 | 6/2011 | Fitzpatrick et al. | |
| 2011/0202089 A1 | 8/2011 | Sun | |
| 2012/0053617 A1 | 3/2012 | Benz et al. | |
| 2012/0116444 A1 | 5/2012 | Zodnik et al. | |
| 2012/0150215 A1 | 6/2012 | Donald | |
| 2012/0191127 A1 | 7/2012 | Guillot | |
| 2012/0191128 A1 | 7/2012 | Teeslink et al. | |
| 2012/0215252 A1 | 8/2012 | Adenmark | |
| 2012/0221041 A1 | 8/2012 | Hansson et al. | |
| 2012/0226306 A1 | 9/2012 | Jackson et al. | |
| 2012/0232579 A1 | 9/2012 | Lee | |
| 2012/0238934 A1 * | 9/2012 | During | A61B 17/1325 602/53 |
| 2012/0271179 A1 | 10/2012 | Adenmark | |
| 2012/0296369 A1 | 11/2012 | Atthoff et al. | |
| 2013/0123836 A1 | 5/2013 | Lampropoulos et al. | |
| 2013/0245674 A1 | 9/2013 | Satoshi et al. | |
| 2014/0012175 A1 * | 1/2014 | Oka | A61F 13/02 602/58 |
| 2014/0012313 A1 | 1/2014 | Finkielsztein et al. | |
| 2014/0018845 A1 | 1/2014 | Lampropoulos et al. | |
| 2014/0031861 A1 | 1/2014 | Teeslink et al. | |
| 2014/0094731 A1 | 4/2014 | Serola | |
| 2014/0142615 A1 | 5/2014 | Corrigan | |
| 2014/0188077 A1 * | 7/2014 | Bakhtyari-Nejad-Esfahani | A61B 17/1322 604/506 |
| 2015/0073326 A1 | 3/2015 | Shih | |
| 2015/0119773 A1 | 4/2015 | Flannery et al. | |
| 2015/0119925 A1 | 4/2015 | Saatchi et al. | |
| 2015/0119926 A1 | 4/2015 | Saatchi et al. | |
| 2015/0201948 A1 | 7/2015 | Kornowski et al. | |

FOREIGN PATENT DOCUMENTS

| | | |
|---|---|---|
| EP | 0837653 | 4/1998 |
| EP | 1382306 | 2/2004 |
| EP | 2070483 | 6/2009 |
| EP | 1455659 | 3/2010 |
| EP | 2245998 | 11/2010 |
| EP | 2647359 | 3/2014 |
| EP | 2677945 | 11/2014 |
| GB | 190912486 | 3/1910 |
| GB | 239717 | 9/1925 |
| JP | 2005318998 | 11/2005 |
| JP | 2012010823 | 1/2012 |
| JP | 2012010825 | 1/2012 |
| JP | 2012034821 | 2/2012 |
| JP | 2012040114 | 3/2012 |
| JP | 2013078529 | 2/2013 |
| JP | 5326160 | 10/2013 |
| JP | 2015066028 | 4/2015 |
| WO | WO2012/129146 | 9/2012 |
| WO | WO2014018280 | 1/2014 |
| WO | WO2014027347 | 2/2014 |
| WO | WO2014075627 | 5/2014 |
| WO | WO2015001198 | 1/2015 |

(56) References Cited

FOREIGN PATENT DOCUMENTS

| WO | WO2015060966 | 4/2015 |
| WO | WO2015060967 | 4/2015 |
| WO | WO2015061016 | 4/2015 |

* cited by examiner

TISSUE COMPRESSION DEVICE WITH FIXATION AND TENSION STRAPS

Tissue compression devices with fixation and tension straps and methods of using the same are described herein.

BACKGROUND

The diagnosis and treatment of coronary artery disease is now often accomplished using vascular delivery apparatus and techniques. Vascular delivery may provide a variety of advantages because access to desired locations within a patient's body may be obtained without the need for general anesthetic or more invasive surgical techniques. Access to peripheral arteries may be accomplished using a sheath having a hemostatic valve that is inserted into the peripheral artery. A catheter or other device can then be introduced into the vasculature of the patient through that sheath to the desired location within the vasculature.

Access for these percutaneous coronary procedures may be obtained through a radial artery of the patient. Access through a radial artery may provide a number of advantages including improved patient mobilization and reduced cost. The use of a distal radial artery may, for example, allow for compression to be directly applied to the artery to achieve and maintain hemostasis.

One potential complication with any arterial access is, however, achieving hemostasis during and/or after a procedure. Arterial blood flow is pulsatile in nature and may present challenges to any practitioner seeking to achieve hemostasis at an arterial access site. Upon completion of a procedure and after removal of a catheter or other device located in the access site, pressure may be applied to the access site to achieve hemostasis and close the access site. Applying pressure at or at a point slightly upstream of the access site is one technique that may be used for achieving hemostasis. In many instances, continuous pressure may be needed to achieve hemostasis at the access site. Although it may be advantageous for the pressure to remain constant, in some instances a reduction in the level of applied pressure may be advantageous after an initially higher level of pressure is applied to the access site. Gradual reduction in the compression pressure may allow blood to flow through the artery of the access site to allow blood to reach tissue downstream from the access site. That blood flowing through the artery can, in some instances, improve clotting to achieve hemostasis without continuing application of compression.

SUMMARY

Tissue compression devices with a combination of fixation and tension straps and methods of using the same are described herein.

The tissue compression devices described herein may, in one or more embodiments, include a combination of fixation and tension straps that are used together to fix or attach the tissue compression device over selected tissue at a selected location on a patient and to apply pressure to the selected tissue. In one or more embodiments, the fixation straps are used to fix or attach the tissue compression device and the tension straps are used to provide tension that is converted to pressure on the selected tissue.

The tissue compression devices and methods described herein may be used to apply pressure to selected tissue at any selected location on a patient, but the tissue compression devices may be particularly well-suited to apply pressure to tissue that includes a radial artery or other blood vessel that may, in one or more embodiments, be used as an access site for a percutaneous procedure. Applying pressure at an access site may provide control over bleeding at that location while still allowing blood flow through the radial artery.

The tissue compression devices described herein include a pressure element having a deformable body and, optionally, a support structure. The deformable body has a skin-facing surface and a back surface. The tissue compression devices described herein are configured such that the skin-facing surface of the deformable body faces the skin over the selected tissue to be compressed when the tissue compression device is in use.

In one or more embodiments of the tissue compression devices described herein, a length adjustment mechanism may be operably attached to the tension straps and configured to adjust the length of the tension straps when the tension straps are connected to each other as a way of adjusting the pressure provided to the selected tissue by the tissue compression devices.

The fixation straps of the tissue compression devices described herein are configured to retain the pressure element at a selected location on a patient before the tension straps are used to adjust the pressure applied to the selected tissue at the selected location. In one or more embodiments, the fixation straps may include pressure sensitive adhesive so that the fixation straps can be adhesively attached to the patient or to each other to retain the pressure element at the selected location.

In a first aspect, one or more embodiments of the tissue compression devices described herein may include: a pressure element comprising a deformable body, wherein the deformable body comprises a skin-facing surface and a back surface on an opposite side of the deformable body from the skin-facing surface; a first tension strap comprising a proximal end attached to and extending away from the first end of the pressure element and a second tension strap comprising a proximal end attached to and extending away from the second end of the pressure element; a connector configured to connect the first and second tension straps to each other such that the connected first and second tension straps define a combined length extending from the first end of the pressure element to the second end of the pressure element that encircles a limb of a patient; a length adjustment mechanism operably attached to the first and/or second tension straps, the length adjustment mechanism configured to adjust the combined length of the connected first and second tension straps when connected to each other; and a first fixation strap extending away from a first end of the pressure element and a second fixation strap extending away from a second end of the pressure element, wherein the first and second fixation straps are configured to retain the pressure element and the first and second tension straps at a selected location on a patient before the first and second tension straps are connected to each other.

In one or more embodiments of tissue compression devices according to the first aspect, the first and second fixation straps comprise pressure sensitive adhesive configured to adhesively attach the first and second fixation straps to skin. In one or more embodiments, the first fixation strap comprises a first release liner positioned over the pressure sensitive adhesive on the first fixation strap, and wherein the second fixation strap comprises a second release liner positioned over the pressure sensitive adhesive on the second fixation strap.

In one or more embodiments of tissue compression devices according to the first aspect, the first and second fixation straps are configured to attach to each other such that the first and second fixation straps encircle a limb of a patient when connected to each other. In one or more embodiments, the first and second fixation straps comprise cohesive material. In one or more embodiments, the first and second fixation straps comprise mechanical fastener materials.

In one or more embodiments of tissue compression devices according to the first aspect, the length adjustment mechanism comprises a ratcheting buckle and ladder strap.

In one or more embodiments of tissue compression devices according to the first aspect, the length adjustment mechanism comprises a captive screw and a cooperating thread pattern.

In one or more embodiments of tissue compression devices according to the first aspect, the connector and the length adjustment mechanism are integrated into a tension mechanism. In one or more embodiments, the tension mechanism comprises a ratcheting buckle attached to the first tension strap and wherein the second tension strap comprises a ladder strap configured to cooperate with the ratcheting buckle. In one or more embodiments, the tension mechanism comprises a captive screw attached to the first tension strap and wherein the second tension strap comprises a cooperating thread pattern.

In one or more embodiments of tissue compression devices according to the first aspect, one or both of the first and second fixation straps exhibit elasticity when placed under tension.

In one or more embodiments of tissue compression devices according to the first aspect, one or both of the first and second tension straps exhibit elasticity when placed under tension.

In one or more embodiments of tissue compression devices according to the first aspect, the first and second fixation straps comprise portions of a unitary fixation strap that extends over the pressure element between the first and second ends of the pressure element such that the skin-facing surface of the deformable body faces away from the unitary fixation strap that extends over the pressure element and the back surface of the deformable body faces the unitary fixation strap that extends over the pressure element.

In one or more embodiments of tissue compression devices according to the first aspect, the first and second tension straps comprise portions of a unitary tension strap that extends over the pressure element between the first and second ends of the pressure element such that the skin-facing surface of the deformable body faces away from the unitary fixation strap that extends over the pressure element and the back surface of the deformable body faces the unitary fixation strap that extends over the pressure element. In one or more embodiments, the unitary tension strap comprises a tension strap window located between the first and second ends of the pressure element.

In one or more embodiments of tissue compression devices according to the first aspect, the pressure element is configured to allow visual access to the selected location on the patient when the pressure element is retained over the selected location by the first and second fixation straps. In one or more embodiments, at least the portion of the deformable body retained over the selected location is transparent. In one or more embodiments, at least the portion of the deformable body and at least the portion of the support structure retained over the selected location are transparent.

In one or more embodiments of tissue compression devices according to the first aspect, the deformable body comprises a resilient gel pad.

In one or more embodiments of tissue compression devices according to the first aspect, the deformable body comprises a fluid-filled bladder.

In a second aspect, one or more embodiments of a method of attaching a tissue compression device as described herein may include: retaining a pressure element over a selected location on a patient using first and second fixation straps to a patient, wherein the first fixation strap extends away from a first end of the pressure element and the second fixation strap extends away from a second end of the pressure element; connecting a first tension strap to a second tension strap after retaining the pressure element over the selected location using the first and second fixation straps, wherein the first tension strap is attached to and extends away from the first end of the pressure element and wherein the second tension strap is attached to and extends away from the second end of the pressure element, and wherein the first and second tension straps define a combined length extending from the first end of the pressure element to the second end of the pressure element that encircles a limb of a patient; and increasing pressure exerted on the selected location by the pressure element by reducing the combined length of the connected first and second tension straps after connecting the first and second straps to each other.

In one or more embodiments of the methods described herein, the method comprises adhesively attaching the first and second fixation straps to skin to retain the pressure element over the selected location.

In one or more embodiments of the methods described herein, the method comprises connecting the first and second fixation straps to each to retain the pressure element over the selected location.

In one or more embodiments of the methods described herein, at least a portion of the first tension strap is located over at least a portion of the first fixation strap, and wherein at least a portion of the second tension strap is located over at least a portion of the second fixation strap after connecting the first tension strap to the second tension strap.

In one or more embodiments of the methods described herein, reducing the combined length of the connected first and second tension straps comprises advancing a ladder strap through a ratcheting buckle.

In one or more embodiments of the methods described herein, reducing the combined length of the connected first and second tension straps comprises rotating a captive screw attached to the first tension strap to advance the second tension strap past the captive screw.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term "comprises" and variations thereof do not have a limiting meaning where these terms appear in the accompanying description. Moreover, "a," "an," "the," "at least one," and "one or more" are used interchangeably herein.

The above summary is not intended to describe each embodiment or every implementation of the tissue compression devices or methods described herein. Rather, a more complete understanding of the invention will become apparent and appreciated by reference to the following Description of Illustrative Embodiments and claims in view of the accompanying figures of the drawing.

DESCRIPTION OF ILLUSTRATIVE EMBODIMENTS

Figure 1:
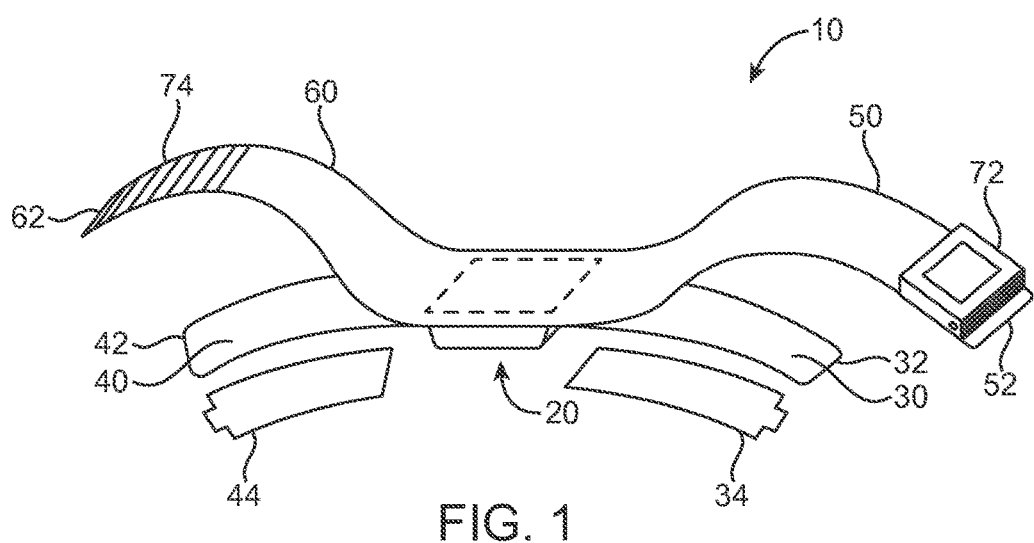
FIG. 1 is a perspective view of one illustrative embodiment of a tissue compression device as described herein.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

Figure 2:
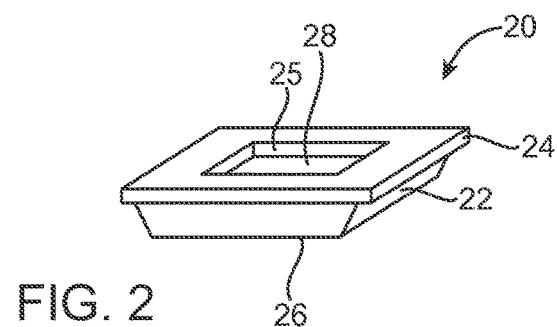
FIG. 2 is an enlarged perspective view of the pressure element of the tissue compression device of FIG. 1 removed from the remainder of the device.

A perspective view of one illustrative embodiment of a tissue compression device 10 as described herein is depicted in FIG. 1. The tissue compression device 10 includes a pressure element 20 which is separately depicted in FIG. 2. The pressure element 20 includes, in one or more embodiments, a deformable body 22 and an optional support structure 24. The deformable body has a skin facing surface 26 and a back surface 28 on an opposite side of the deformable body 22. The back surface 28 of the deformable body 22 is attached to the support structure 24 to provide mechanical support (e.g., in the form of a frame, base, etc.) to the deformable body 22 of the pressure element 20. Although depicted as separate components, in one or more embodiments the deformable body 22 and the support structure 24 may be provided as an integrated unit.

In one or more embodiments, the support structure 24 may include an optional window or opening 25 in which the back surface 28 of the deformable body 22 is exposed. This feature may, in one or more embodiments, allow for visualization of tissue over which the pressure element 20 is located as described herein (where, e.g., the deformable body 22 is transparent). In one or more alternative embodiments, however, the support structure 24 may itself be transparent such that visualization of tissue located beneath the skin facing surface 26 of the deformable body 22 may be seen through the support structure 24 as well as the deformable body 22 (where, e.g., the deformable body 22 is transparent). In such an arrangement, the support structure 24 may not require a window or opening 25.

In one or more embodiments, the deformable body 22 may have a default or normal shape when the deformable body is not subjected to any external force (other than gravity) and be configured to conform to a surface against which it is compressed. The resilient nature of the deformable body may be elastic, i.e., in the absence of external forces on the deformable body 22, it may, over a relatively short period of time, e.g., 5 minutes or less, return to its default or normal shape.

In one or more embodiments, the deformable body 22 may be in the form of a resilient pad that is capable of deforming to conform to the shape of a surface against which it is compressed. In one or more embodiments, the resilient pad of the deformable body 22 may include a variety of one or more resilient, conformable materials, e.g., gels, foams, etc. In one or more alternative embodiments, the deformable body 22 may be in the form of a fluid-filled bladder where the fluid may include one or more liquids and/or gases. In one or more embodiments in which the deformable body is in the form of a fluid-filled bladder, the volume of fluid in the bladder may be adjusted (i.e., increased and/or decreased) using, e.g., a syringe, pump, etc.

In one or more embodiments, the tissue compression devices described herein may also include a first fixation strap 30 extending away from a first end of the pressure element 20 and a second fixation strap 40 extending away from a second end of the pressure element 20 such that the first and second fixation straps 30 and 40 extend away from opposite ends of the pressure element 20. The first fixation strap 30 has a distal end 32 located furthest away from the pressure element 20 and the second fixation strap 40 has a distal end 42 located furthest away from the pressure element 20. One or both of the fixation straps 30 and 40 may be constructed to be extensible in use (i.e., such that the length of the strap increases in response to tension forces) or inextensible (i.e., such that the length of the strap does not increase in response to tension forces applied during normal use of the tissue compression devices described herein).

The first and second fixation straps 30 and 40 of the tissue compression device 10 are configured to retain the pressure element 20 on a patient. In the illustrative embodiment depicted in FIG. 1, the first and second fixation straps 30 and 40 may include pressure sensitive adhesive located on a skin facing surface (not seen in the view of FIG. 1) similar to, e.g., the use of pressure sensitive adhesive on a medical adhesive bandage. In one or more embodiments, the tissue compression device 10 may include a release liner 34 located over the pressure sensitive adhesive on first fixation strap 30 to protect the pressure sensitive adhesive located thereon before use (the liner 34 is depicted in FIG. 1 as being removed from the first fixation strap 30). In one or more embodiments, the tissue compression device 10 may also include a release liner 44 located over the pressure sensitive adhesive on second fixation strap 42 protect the pressure sensitive adhesive located thereon before use (the liner 44 is also depicted in FIG. 1 as being removed from the second fixation strap 40).

Although the pressure sensitive adhesive used on the first and second fixation straps 30 and 40 may be designed to, in one or more embodiments, attach the straps to the skin of a patient, in one or more alternative embodiments, the straps 30 and 40 may include adhesive that is adapted to attach the straps 30 and 40 to each other such that the adhesive does not contact the skin of a patient.

The tissue compression devices described herein also include, in one or more embodiments, first and second tension straps. In the illustrative embodiment of tissue compression device 10 depicted in FIG. 1, a first tension strap 50 is attached to the pressure element 20 and extends away from a first end thereof and a second tension strap 60 is attached to the pressure element 20 and extends away from an opposite end of the pressure element 20. The first tension strap 50 includes a distal end 52 located furthest away from the pressure element 20 and the second tension strap 60 includes a distal end 62 located furthest away from the pressure element 20.

In the tissue compression devices described herein, the first and second fixation straps 30 and 40 are used to retain or fix the pressure element 20 at a selected location on a patient before the first and second tension straps 50 and 60 are placed in tension around a limb of a patient, with that tension force being converted to a compression at the pressure element 20.

To supply tension, the first and second tension straps 50 and 60 are connected to each other such that, when connected, the first and second tension straps 50 and 60 define a combined length extending from the first end of the pressure element 20 (where the first tension strap 50 extends away from the pressure element 20) to a second end of the pressure element 20 (where the second tension strap 60 extends away from the pressure element 20). That combined length of the first and second tension straps 50 and 60 is configured to encircle a limb of a patient when the tissue compression device is in use.

In one or more embodiments, the first tension strap 50 and/or the second tension strap 60 may exhibit elasticity such that the length of the strap increases when placed in tension around a limb of a patient. Any tension strap that exhibits elasticity such that the length of the strap increases as described herein may return to at or near its original length (i.e., its length before being extended under tension) over a relatively short period of time when the tension force is removed. In one or more alternative embodiments, however, the first and second tension straps 50 and 60 may be inextensible in normal use under the tension forces needed to supply the desired tissue compression using tissue compression devices as described herein.

In one or more embodiments, the tissue compression devices described herein may include a connector that is configured to connect the first tension strap 50 to the second tension strap 60 such that the first and second tension straps 50 and 60 define the combined length described herein. In the illustrative embodiment of tissue compression device 10 depicted in FIG. 1, the connector may take the form of a ratcheting buckle 72 located on the first tension strap 50 and a ladder strap 74 located on the second tension strap 60.

The tissue compression devices described herein also include, in one or more embodiments, a length adjustment mechanism operably attached to one or both of the first and second tension straps 50 and 60. The length adjustment mechanism is configured to adjust the combined length of the first and second tension straps 50 and 60 when those straps are connected to each other. In one or more embodiments, the length adjustment mechanism can be used to both shorten and lengthen and the combined length of the tension straps 50 and 60. As the length adjustment mechanism is used to reduce the combined length of the first and second tension straps 50 and 60 when those straps are connected to each other to encircle a limb, the tension in the combined straps is increased. That decreasing length and corresponding tension increase is converted to a compressive force by the pressure element 20.

In the illustrative embodiment of tissue compression device 10 as depicted in FIG. 1, the ratcheting buckle 72 and ladder strap 74 serve as both the connector of the first and second tension straps 50 and 60, as well as the length adjustment mechanism that is configured to adjust the combined length of the connected first and second tension straps 50 and 60. Such dual functionality, i.e., where the same mechanism is used to both connect the tension straps and adjust the combined length of the tension straps is not, however, required in tissue compression devices as described herein.

Although one or more embodiments of tissue compression devices as described herein may include ratcheting buckles and ladder straps, many other different mechanisms may be used to provide the length adjustment mechanism and/or connectors in tissue compression devices as described herein.

Figure 3:
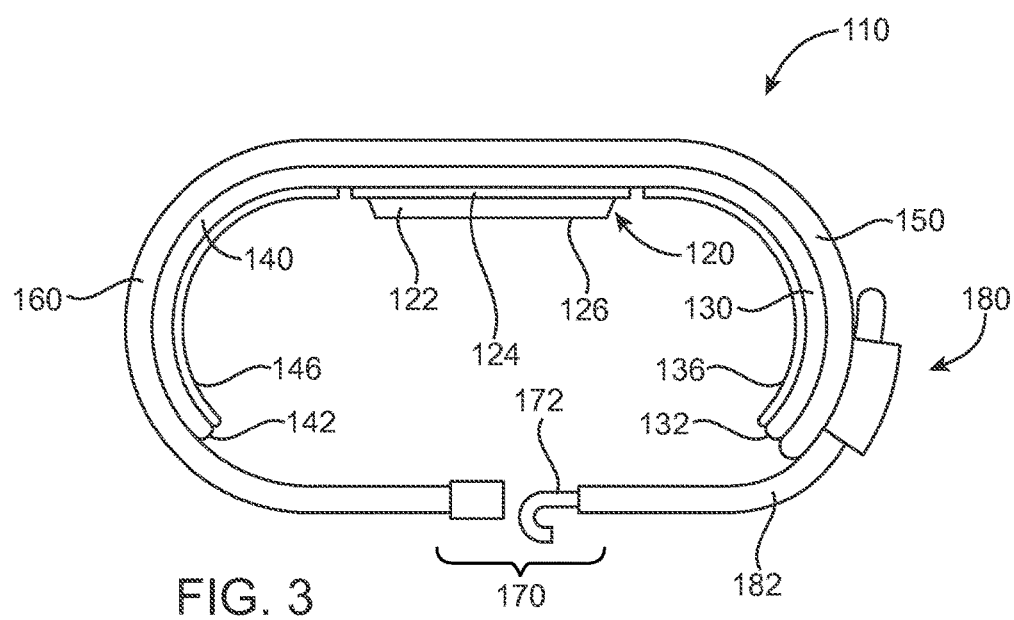
FIG. 3 is a side view of another illustrative embodiment of a tissue compression device as described herein.
Figure 4:
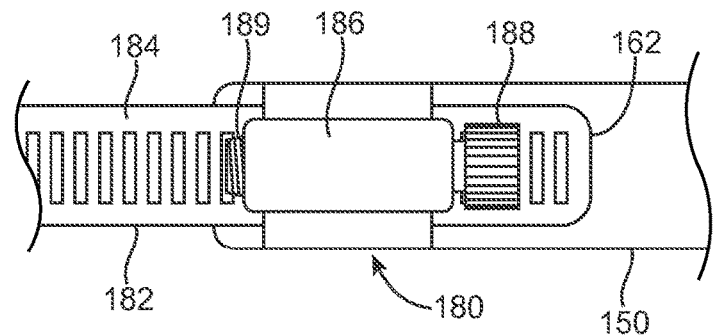
FIG. 4 is an enlarged perspective view of the illustrative embodiment of the length adjustment mechanism used in the embodiment of the tissue compression device of FIG. 3.
Figure 5:
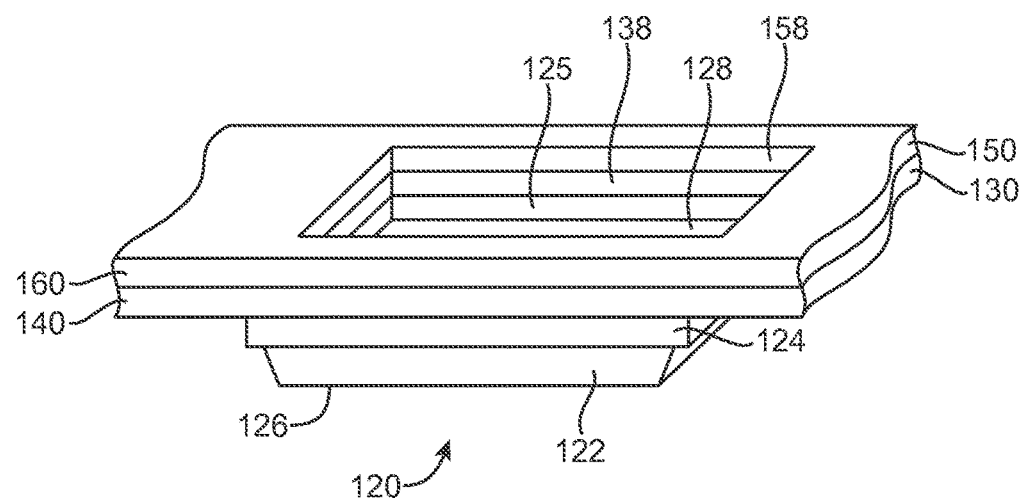
FIG. 5 is an enlarged perspective view of the portion of the tissue compression device depicted in FIG. 3, with the portion including the pressure element of the tissue compression device.

Another illustrative embodiment of a tissue compression device as described herein is depicted in connection with FIGS. 3-5. The tissue compression device 110 includes a pressure element 120, as well as a first fixation strap 130 extending away from a first end of the pressure element 120 and a second fixation strap 140 extending away from a second end of the pressure element 120. Also seen in FIG. 3 is a layer of pressure sensitive adhesive 136 on the first fixation strap 130 and a layer of pressure sensitive adhesive 146 on the second fixation strap 140. The tissue compression device 110 also includes a first tension strap 150 extending away from a first end of the pressure element 120 and a second tension strap 160 extending away from a second end of the pressure element 120.

In the depicted embodiment of tissue compression device 110, the first and second fixation straps 130 and 140 will not typically be long enough such that their distal ends 132 and 142, respectively, meet when the tissue compression device 110 is in a selected location on a patient. As a result, the fixation straps 130 and 140 and the pressure sensitive adhesive located thereon is used to retain the pressure element 120 on a selected location of a patient before the first and second tension straps 150 and 160 are connected to each other as described herein. As a result, the fixation straps 130 and 140 may be described as also retaining the first and second tension straps 150 and 160 on the patient before they are connected to each other as described herein.

In the illustrative embodiment of tissue impression device 110 as depicted in FIG. 3, a connector 170 connects the first tension strap 150 to the second tension strap 160 such that the connected first and second tension straps 150 and 160 define a combined length extending from the first end of the pressure element 120 to the second end of the pressure element 120. The illustrative embodiment of connector 170 is in the form of a hook 172 on strap 150 that connects to a slot or opening (not shown) in the opposing component on the strap 160. The hook is, in the depicted embodiment, located at a distal end of the first tension strap 150 and the opposing component containing a slot or opening to receive the hook being located at a distal end of the second tension strap 160.

Unlike the ratcheting buckle and ladder strap mechanism used in connection with the illustrative embodiment of tissue compression device 10 as depicted in FIG. 1, the connector 170 does not also function as a length adjustment mechanism used to adjust the combined length of the first and second tension straps 150 and 160. Rather, in the illustrative embodiment of tissue compression device 110, a length adjustment mechanism 180 is separate from the connector 170. In the depicted embodiment, the length adjustment mechanism 180 is in the form of a captive screw and cooperating thread pattern that is depicted in an enlarged view in FIG. 4.

The length adjustment mechanism 180 includes a housing 186 attached to one of the tension straps (i.e., tension strap 150 in the depicted embodiment). The housing 186 contains a screw 188 captured therein with the screw including threads 189 that cooperate with a thread pattern in the form of slots 184 on strap 182 that forms a portion of the first tension strap 150.

Rotation of the screw 188 can be used to adjust the length of first tension strap 150 such that, when the first tension strap 150 is connected to the second tension strap 160 to form a combined length as described herein, adjustment of the length of the first tension strap 150 also adjusts the combined length of the first and second tension straps 150 and 160.

In one or more alternative embodiments, the length adjustment mechanism 180 may also function as a connector, although such an arrangement would require threading of the portion of the second tension strap 160 containing the slots forming the thread pattern 184 with the screw 188 to connect the first and second tension straps 150 and 160 to each other. Such a requirement may, in one or more embodiments, make connection of the first and second tension straps 150 and 160 to each other possible, but potentially cumbersome.

Another optional feature that may be included in one or more embodiments of the tissue compression devices described herein is depicted in the perspective view of FIG. 5 and relates to the illustrative embodiment of pressure element 120 in the tissue compression device 110 of FIG. 3. The depicted pressure element 120 includes a deformable body 122 with a skin facing surface 126 and a support structure 124 attached to the deformable body 122. In the depicted illustrative embodiment, the first fixation strap 130 and the second fixation strap 140 which extend away from opposite ends of the pressure element 120 are portions of a unitary fixation strap that extends over the pressure element 120 between the opposing ends of the pressure element 120 such that the support structure 124 is located between the unitary fixation strap and the deformable body 122. Alternatively, the fixation straps 130 and 140 may, in fact, be separate straps attached to opposite ends of the pressure element 120.

Yet another optional feature also depicted in the perspective view of FIG. 5 of the illustrative embodiment of pressure element 120 in the tissue compression device 110 of FIG. 3 is a unitary tension strap. The first tension strap 150 and the second tension strap 160 extend away from opposite ends of the pressure element 120 and are, in essence, formed of portions of the unitary tension strap which extends over the pressure element 120. Alternatively, the tension straps 150 and 160 may, in fact, be separate straps attached to opposite ends of the pressure element 120.

In embodiments in which a unitary strap is used for one or both of the tension and fixation straps as depicted in, e.g., FIG. 5, the unitary straps may, in one or more embodiments, include windows or openings to allow visualization of the back surface 128 of the deformable body 122. In particular, opening or window 125 may be formed in the support structure 124, opening or window 138 may be found in the unitary strap forming the fixation straps 130 and 140, and opening or window 158 may be found in the unitary strap forming the tension straps 150 and 160. Alternatively, any straps and/or support structure extending over the back of the pressure element 120 may be constructed of materials that allow for visual observation of the tissue located beneath the pressure element 120.

Figure 6:
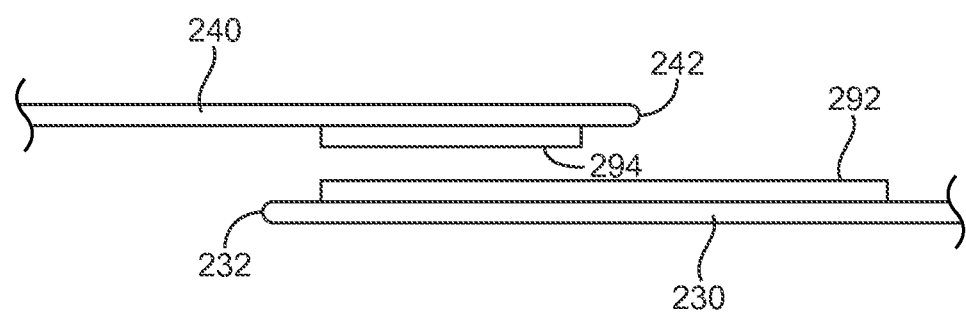
FIG. 6 depicts another illustrative embodiment of materials that can be used to connect the tension and/or fixation straps in connection with tissue compression devices as described herein.

FIG. 6 depicts another illustrative embodiment of strap connections that may be used to connect tension and/or fixation straps in one or more embodiments of the tissue compression devices as described herein. In particular, a portion of the distal end of a first fixation strap 230 including the distal end 232 of the strap 230 is depicted in FIG. 6 along with a portion of the distal end of a second fixation strap 240 including its distal end 242. Unlike the fixation straps depicted in the illustrative embodiments of tissue compression devices as seen in FIGS. 1 and 3, the fixation straps 230 and 240 are sufficiently long to encircle the limb of a patient on which the tissue compression device is attached. As a result, the fixation straps 230 and 240 may be attached to each other rather than being attached directly to the patient. In the illustrative embodiment depicted in FIG. 6, first fixation strap 230 includes connection material 292 while second fixation strap 240 includes connection material 294. In one or more embodiments, the connection material 292 and 294 may be in the form of, e.g., cohesive materials, hook and loop closure materials, interlocking mechanical fastener materials, etc.

Although depicted in connection with fixation straps 230 and 240, it will be understood that this technique of connecting straps may be used with the tension straps of one or more embodiments of tissue compression devices as described herein—provided that the connection formed by the connection materials has sufficient strength to hold the straps together when under tension.

Although illustrative embodiments of pressure elements that may be used in a tissue compression device including fixation and tension straps are described herein, the tissue compression devices may use many different pressure elements in place of the illustrative embodiments described herein. Some examples of potentially useful pressure elements that may be used with the fixation and tension strap arrangements described herein are the apparatus designed to compress tissue as described in connection with U.S. Pat. No. 7,498,477 (see, e.g., the fluid-filled bladders and related structure in, e.g., FIG. 2), U.S. Pat. No. 8,353,927 (see, e.g., the pad 36 and related structure in, e.g., FIG. 3), U.S. Patent Application Publication No. 2012/0191127 (see, e.g., the pressure element 14 and related structure in, e.g., FIG. 4a). Still other potentially useful pressure elements that may be used with the fixation and tension strap arrangements described herein are the apparatus designed to compress tissue as described in, e.g., co-pending U.S. patent application Ser. No. 14/261,771, titled TISSUE COMPRESSION DEVICE WITH MULTI-CHAMBER BLADDER (filed on Apr. 25, 2014), as well as the deflecting pressure elements described in, e.g., co-pending U.S. patent application Ser. No. 14/262,316, titled TISSUE COMPRESSION DEVICE WITH DEFLECTING PRESSURE ELEMENT.

The complete disclosure of the patents, patent documents, and publications identified herein are incorporated by reference in their entirety as if each were individually incorporated. To the extent there is a conflict or discrepancy between this document and the disclosure in any such incorporated document, this document will control.

Illustrative embodiments of the tissue compression devices or methods are discussed herein some possible variations have been described. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof. It should also be understood that this invention also may be suitably practiced in the absence of any element not specifically disclosed as necessary herein.

What is claimed is:

1. A tissue compression device comprising:
a pressure element having first and second ends;
a first tension strap comprising a proximal end attached to and extending away from the first end of the pressure element and a second tension strap comprising a proximal end attached to and extending away from the second end of the pressure element;
a connector configured to connect the first and second tension straps to each other such that the connected first and second tension straps define a combined length extending from the first end of the pressure element to the second end of the pressure element;
a first fixation strap including a first strap distal end extending away from the first end of the pressure element and a second fixation strap including a second strap distal end extending away from the second end of the pressure element, wherein the first and second fixation straps are configured to retain the pressure element and the first and second tension straps at a selected location on a patient before the first and second tension straps are connected to each other, wherein the first and second fixation straps include a pressure sensitive adhesive configured to adhesively attach the first and second fixation straps to skin of the patient or wherein the first and second strap distal ends are adapted to attach to each other, wherein the first strap distal end and the second strap distal end are free ends that are not coupled to the first tension strap and the second tension strap, respectively; and
a length adjustment mechanism operably attached to the first and/or second tension straps, the length adjustment mechanism configured to adjust the combined length of the connected first and second tension straps when connected to each other such that pressure applied by the pressure element to the selected location is increased by reducing the combined length and decreased by increasing the combined length,
wherein when the first and second tension straps are connected to each other, an outer surface the first fixation strap is in contact with an inner surface of the first tension strap and an outer surface of the second fixation strap is in contact with an inner surface of the second tension strap.

2. The device according to claim 1, wherein the first and second fixation straps comprise the pressure sensitive adhesive configured to adhesively attach the first and second fixation straps to skin.

3. The device according to claim 2, wherein the first fixation strap comprises a first release liner positioned over the pressure sensitive adhesive on the first fixation strap, and wherein the second fixation strap comprises a second release liner positioned over the pressure sensitive adhesive on the second fixation strap.

4. The device according to claim 1, wherein the first and second fixation straps are configured to attach to each other such that the first and second fixation straps encircle a limb of the patient when connected to each other.

5. The device according to claim 4, wherein the first and second fixation straps comprise connection material.

6. The device according to claim 1, wherein the length adjustment mechanism comprises a ratcheting buckle and ladder strap.

7. The device according to claim 1, wherein the length adjustment mechanism comprises a captive screw and a cooperating thread pattern.

8. The device according to claim 1, wherein the connector and the length adjustment mechanism are integrated into a tension mechanism.

9. The device according to claim 8, wherein the tension mechanism comprises a ratcheting buckle attached to the first tension strap and wherein the second tension strap comprises a ladder strap configured to cooperate with the ratcheting buckle.

10. The device according to claim 8, wherein the tension mechanism comprises a captive screw attached to the first tension strap and wherein the second tension strap comprises a cooperating thread pattern.

11. The device according to claim 1, wherein one or both of the first and second fixation straps exhibit elasticity when placed under tension.

12. The device according to claim 1, wherein one or both of the first and second tension straps exhibit elasticity when placed under tension.

13. The device according to claim 1, wherein the pressure element is a deformable body configured to allow visual access to the selected location on the patient when the pressure element is retained over the selected location by the first and second fixation straps.

14. The device according to claim 13, wherein at least the portion of the deformable body retained over the selected location is transparent.

15. The device according to claim 13, wherein at least a portion of the deformable body and at least a portion of the support structure retained over the selected location are transparent.

16. The device according to claim 13, wherein the deformable body comprises a resilient pad.

17. The device according to claim 13, wherein the deformable body comprises a fluid-filled bladder.

18. A tissue compression device comprising:
a pressure element having first and second ends, the pressure element comprising a skin-facing surface and a back surface on an opposite side of the pressure element from the skin-facing surface;
a unitary fixation strap that extends over the pressure element between the first and second ends of the pressure element such that the skin-facing surface faces away from the unitary fixation strap that extends over the pressure element, and the back surface faces the unitary fixation strap that extends over the pressure element, the unitary fixation strap having a first fixation strap end extending away from the first end of the pressure element and a second fixation strap end extending away from the second end of the pressure element;
a unitary tension strap that extends over the unitary fixation strap for the entire length of the unitary fixation strap such that the skin-facing surface faces away from the unitary tension strap and the unitary fixation strap is disposed between the unitary tension strap and the pressure element, the unitary tension strap having a first tension strap end extending away from the first end of the pressure element and a second tension strap end extending away from the second end of the pressure element;
a connector configured to connect the first and second tension strap ends to each other such that the connected unitary fixation strap defines a combined length extending from the first end of the pressure element to the second end of the pressure element; and
a length adjustment mechanism operably attached to the unitary tension strap, the length adjustment mechanism configured to adjust the combined length of the connected unitary tension strap when the first and second tension strap ends are connected to each other such that pressure applied by the pressure element to the selected location is increased by reducing the combined length and decreased by increasing the combined length, wherein the unitary fixation strap is configured to retain the pressure element and the unitary tension strap at a selected location before the first and second tension strap ends are connected to each other, wherein the first and second fixation strap ends are free ends that are not coupled to the unitary tension strap, and wherein the unitary fixation strap includes a pressure sensitive adhesive configured to adhesively attach the unitary fixation strap to skin of a patient or wherein the first and second fixation strap ends are adapted to attach to each other.

19. The device according to claim 18, wherein the pressure element is transparent, and further wherein the unitary fixation and tension straps comprise windows located between the first and second ends of the pressure element to view the transparent pressure element.

20. The device according to claim 18, wherein the connector and the length adjustment mechanism are integrated into a tension mechanism.

* * * * *